United States Patent [19]

Welch

[11] Patent Number: 4,672,951
[45] Date of Patent: Jun. 16, 1987

[54] METHOD AND APPARATUS FOR TREATMENT OF BIOLOGICAL TISSUE

[75] Inventor: Albert B. Welch, Dallas, Tex.
[73] Assignee: Bio-Electric, Inc., Knoxville, Tenn.
[21] Appl. No.: 814,255
[22] Filed: Dec. 30, 1985
[51] Int. Cl.$^4$ .............................................. A61N 1/40
[52] U.S. Cl. ................................... 128/1.5; 128/82.1; 128/419 F; 128/421
[58] Field of Search ................................. 128/1.3–1.5, 128/419 F, 82.1, 421–423

[56] References Cited

U.S. PATENT DOCUMENTS

| 3,890,953 | 6/1975 | Kraus et al. | 128/1.5 |
| 4,095,588 | 6/1978 | Goldman et al. | 128/1.5 |
| 4,315,503 | 2/1982 | Ryaby et al. | 128/419 F |

FOREIGN PATENT DOCUMENTS

| 0011019 | 5/1980 | European Pat. Off. | 128/1.5 |
| 0144920 | 6/1985 | European Pat. Off. | 128/1.5 |
| 2736345 | 2/1979 | Fed. Rep. of Germany | 128/1.5 |
| 3042751 | 5/1982 | Fed. Rep. of Germany | 128/419 F |
| 1595108 | 8/1981 | United Kingdom | 128/1.5 |
| 2143131A | 2/1985 | United Kingdom | 128/1.5 |

OTHER PUBLICATIONS

PCT WO82/01135, 4–1982, Rosengant.
Herbst, Elec. Stim. of Bone Growth and Repair, F. Burny et al., edit, Springer-Verlag, Berlin and N.Y., 1978, pp. 1–13.

Primary Examiner—Kyle L. Howell
Assistant Examiner—John C. Hanley
Attorney, Agent, or Firm—Harold E. Meier

[57] ABSTRACT

The treatment of biological tissue is effected by a pulsed electric field induced by a time changing magnetic field produced by a magnetic coil or a plurality of magnetic coils. These magnetic coils are arranged in the area of desired treatment and respond to a driving current to induce the pulsed electric field into the localized treatment area. The driving current and concomitant magnetic field generates an electric field waveform that has a first pulse in a positive direction having a selected value followed by a second pulse in a negative direction having a larger value than the first pulse, and in turn followed by a third pulse in the positive direction having a value on the order of the first pulse. The apparatus for applying the driving current includes switching circuitry for energizing the magnetic coils in pairs to induce a symmetrical distribution of the magnetic and electric fields in the treatment area. This achieves time averaged uniformity of the pulse electric field in the tissue for applications such as stimulation of osteogenesis in long bone nonfusions.

16 Claims, 7 Drawing Figures

METHOD AND APPARATUS FOR TREATMENT OF BIOLOGICAL TISSUE

BACKGROUND OF THE INVENTION

The present invention relates to a method and apparatus for treatment of biological tissues of a living body and more particularly to a medical apparatus and method for pulsed electric field treatment induced by a time varying magnetic field.

Heretofore there has been considerable activity in medical research into the use of direct current, alternating current and pulse signals of single and double polarity in the treatment of biological tissues of living bodies. These research activities have included invasive treatments that utilize implanted electrodes as well as noninvasive techniques utilizing capacitively or inductively coupled induced electric fields. That electric fields stimulate biological changes other than nerve action potentials or thermal effects, which effects occur at much higher field intensities, has previously been demonstrated by producing polarity-selective bone growth and resorption.

In accordance with the present invention, non-invasive techniques are utilized to induce a pulsed electric field in the presence of a concomitant magnetic field to stimulate tissue regeneration or resorption in ordered biological structures, such as bone, or to stimulate cellular chemistry modifications of non-ordered biological structures as found in blood or blood serum. The use of induced, rather than conducted, electric fields for stimulation of osteogenesis has been disclosed in the U.S. Pat. No. 3,893,462 issued to Michael P. Manning. Specific waveform induced electric field strength and pulse repetition patterns using a time varying magnetic field for the treatment of living tissue and/or cells has been disclosed in the U.S. Pat. No. 4,105,017 issued to John P. Ryaby. In accordance with the disclosure in each of these United States patents, the particular field patterns utilized have been shown to require treatment times of several hours per day extending over a period of months. Further, the coil currents required to achieve the stated induced electric fields with the waveforms disclosed in these patents require the use of heavy treatment coils to avoid excessive heating and the consumption of excessive amounts of power through dissipation of the magnetic field energy of the coils. This severely restricts the range of electric field strengths and waveform durations available for treatment and further inhibits the portability of the apparatus. Furthermore, the orientation of the magnetic field and the concomitant induced electric field is spatially fixed and therefore cannot provide symmetrical or uniform stimulation of the treated region. As a result, unwanted spurious growths are often observed after the successful treatment of the original fracture area.

A still further drawback of known techniques for noninvasive treatment utilizing induced electric fields is the potential hazard of electric shock inherent with the large energy storage in high voltage capacitors associated with the waveforms and levels of stimulation.

While it has been recognized and established through research and clinical evaluation that a change in an electrical and/or electromechanical environment of a living cell and/or tissue produces a therapeutic effect on growth, repair and maintenance behavior of the tissue and/or cell, there has not been a general acceptance of such techniques within the medical community. The invasive techniques which implanted electrodes had serious side effects that all but eliminated these techniques. Surgically noninvasive direct inductive coupling, on the other hand, has met with some success and is now being seriously considered by the medical profession. However, there still remains objections to the use of direct inductive coupling primarily for the reasons previously discussed, in particular, the power requirement, weight, and shock hazard. The present invention provides for noninvasive induced pulsed electric fields and conmitant magnetic fields that minimize these disadvantages as found in systems heretofore considered by the medical profession.

SUMMARY OF THE INVENTION

In accordance with the present invention there is provided a method of noninvasive treatment of biological tissue and/or cells wherein a driving current is generated in a coil and, in response thereto, a time changing magnetic field induces a pulsed electric field into a localized treatment area. The improvement of the present invention is to induce a pulsed electric field that produces a waveform having a first pulse in a first direction having a selected value, followed by a second pulse in a second direction having a second value larger than the value of the first pulse and followed by a third pulse in the first direction having a value on the order of the first pulse, and wherein this waveform repeats for a selected number of periods.

More specifically in accordance with the present invention, a pulsed electric field is induced into the biological tissue to be treated by the use of properly positioned coils connected to a switched bipolar current source. The waveform of the pulsed electric field has three identifiable parts including the first pulse in the first direction, a second pulse in the second direction and a third pulse also in the first direction. The magnetic field generated around the coils follows the bipolar current to induce into the treatment area a three-part waveform electric field. Thus, the induced electric field is the time derivative of the driving current with a resulting waveform as previously described.

The present invention utilizes the volt-second product of the individual pulses of the three-part waveform to artificially stimulate healing in cells or tissue of a living body. Specifically, the sum of the volt-second products of the first and third pulses of the waveform equals magnitude of the the volt-second product of the second pulse of the waveform. This is in contrast with heretofore generated waveforms that exbibit only two pulses, one of each polarity, where the first pulse has a small value and long time interval followed by a second pulse having a large value and a short interval or vice versa.

Further in accordance with the present invention, the effective power requirements of a three-pulse waveform are measurably lower than previous systems utilizing a two-pulse waveform. These power requirements are further reduced in the present invention by recycling the energy stored in the magnetic field of the treatment coils between energy storing devices.

In a preferred embodiment of the invention, this switching is accomplished by solid state elements that consume negligible power. When axial symmetry of the induced electric field stimulation is desired, such as in the treatment of a long bone nonfusion, the time changing magnetic field is generated by means of three coils arranged at equal angles around a desired axis of symmetry. These three coils are driven as sequential pairs with fields aiding on each driven pair. The coils are driven in a rotating sequence such that the magnetic field, and as a consequence the orthogonal induced electric field, is rotated through 120 degrees as each sequential pair of coils is driven. This produces a time-averaged symmetry of stimulation.

Also in accordance with the present invention, there is provided apparatus for the non-invasive treatment of biological living tissues and/or cells which apparatus includes a generator of bipolar driving currents. Means responsive to the bipolar driving currents induce a pulsed electric field into a localized treatment area. This means for inducing a pulsed electric field includes means for generating an electric field waveform that has a first pulse in a first direction having a selected value followed by a second pulse in a second direction having a second value larger than the value of the first pulse, and followed by a third pulse in the first direction on the order of the value of the first pulse. Further, there is provided means to couple the energy of the first pulse to generate the second pulse and couple the energy from the second pulse to generate the third pulse and to recover and store this energy for subsequent pulses.

BRIEF DESCRIPTION OF THE DRAWINGS

A more complete understanding of the invention and its advantages will be apparent from the following detailed description taken in conjunction with the accompanying drawings.

Referring to the drawings.

DETAILED DESCRIPTION

Figure 1A:
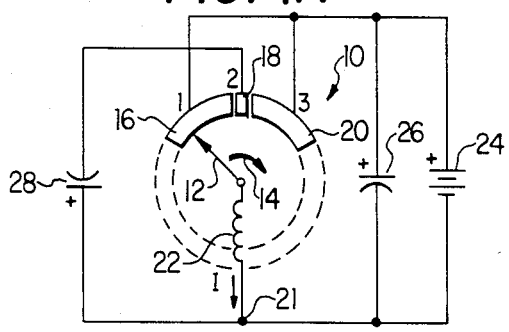
FIG. 1A is a simplified schematic for describing the generation of the induced three-part waveform induced electric field including circuitry for recycling magnetic field energy.

Referring to FIG. 1A there is shown a simplified schematic of apparatus for inducing a three-part electric field into a localized treatment area. A high speed rotary switch 10 includes a wiper arm 12 driven in a clockwise direction as shown by the arrow 14. The rotary arm 12 wipes over three contact segments, 16, 18 and 20 to generate a three-pulse induced electric field by means of a treatment coil 22 having an inductance "L". Each of the contact segments 16, 18 and 20 forms a sector of a circle to establish the time duration for each pulse of the generated waveform.

Connected to the contact segments 16 and 20 is one terminal of a power supply 24 and one terminal of a recycling capacitor 26. The second terminals of the power supply 24 and the recycling capacitor 26 are connected to the treatment coil 22 at connection 21. Also connected to the treatment coil 22 at the connection 21 is one terminal of a recycling capacitor 28 which has a second terminal tied to the contact segment 18.

As the wiping arm 12 is rotated in the direction of the arrow 14 it sequentially connects the treatment coil 22 to each of the contact segments 16, 18 or 20. When connected to the contact segments 16 and 20 the treatment coil 22 is tied to the positive terminal of the recycling capacitor 26 and the positive terminal of the power supply 24. With the treatment coil 22 connected to the contact segment 18 the coil is tied to the negative terminal of the recycling capacitor 28. When the wiper arm 12 passes from the contact segment 20, the treatment coil 22 is disconnected from all sources of energy and the induced electric field decays to zero until the wiper arm again rotates to make contact with the segment 16.

During the time interval when the wiper arm 12 is between the end of the contact segment 20 and the beginning of the contact segment 16 the recycling capacitors 26 and 28 maintain a charge as previously established by the power supply 24.

Figure 1B:
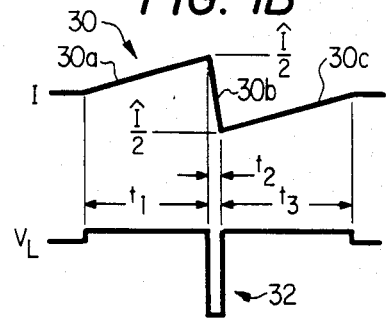
FIG. 1B illustrates the current waveform for generating the three-part waveform of the pulsed electric field as also illustrated.

As the wiper arm 12 rotates between the contact segments 16, 18 and 20 a bipolar driving current is generated as illustrated by the idealized waveform 30 of FIG. 1B. This waveform illustrates the flow of current "I" as measured in the treatment coil 22. As the current is illustrated by the waveform 30 flows through the treatment coil 22 an induced voltage $V_L$ appears across the coil. The waveform of this induced voltage and that induced in the treated tissue is illustrated by the waveform 32 of FIG. 1B.

As the wiper arm 12 first contacts the segment 16 the flow of current "I" in the treatment coil 22 begins to rise along a linear ramp at a rate $dI/dt$ that is equal to the ratio $V_L/L$. This is illustrated by the waveform segment 30a during the time $t_1$ which corresponds to the time the coil 22 is connected to the contact segment 16. That is, the length of the contact segment 16 establishes the time interval $t_1$. With the treatment coil 22 connected to the contact segment 16 the recycling capacitor 26 is discharged through the coil until the wiper arm moves off of the segment 16. At this time, the current "I" has increased to a value $\hat{I}/2$ and the treatment coil 22 is abruptly switched to the recycling capacitor 28 by the wiper arm 12 making contact with the contact segment 18. The current "I" in the treatment coil 22 continues to have a positive value as the recycling capacitor 28 is charged from the energy stored in the coil 22. The coil current continues in a positive direction until the energy that was stored in the magnetic field of the coil has been transferred to the recycling capacitor 28 (neglecting resistance losses). At this point the direction of current flow within the treatment coil 22 reverses to increase in a negative direction by discharging the capacitor 28 until the current reaches a negative peak value of $-\hat{I}/2$. This negative peak value is reached when the wiper arm 12 rotates from the contact segment 18 and contacts the segment 20 and takes place during time $t_2$. The coil has now been abruptly switched back to the recycling capacitor 26. While the wiper arm 12 was in contact with the contact segment 18 the waveform 30b of FIG. 1B illustrates the current flowing in the treatment coil 22.

As the wiper arm 12 contacts the segment 20 the treatment coil 22 is again reconnected to the recycling capacitor 26. However, the current flow is still in the negative direction but decreasing in magnitude along a linear ramp toward the zero axis. During this time interval $t_3$ the stored energy of the magnetic field on the coil 22 is recycled to charge the capacitor 26 until the current has returned to zero. The treatment coil 22 is disconnected by the wiper arm 12 leaving the contact segment 20. The time interval while recycling the energy of the magnetic field in the coil 22 into the recycling capacitor 26 is given by the interval $t_3$. That is, the time $t_3$ is established by the amount of time the wiper arm 12 wipes over the contact segment 20. The treatment coil 22 remains disconnected until the wiper arm 12 again makes contact with the contact segment 16 and the sequence repeats generating another section of the current waveform 30.

With reference to the waveform 32 of FIG. 1B, the induced voltage in the treatment coil 22 is the time derivative of the changing coil current I. This induced voltage generates a time changing magnetic field to induce pulsed electric fields into a localized treatment area. The induced pulsed electric field will have a waveform substantially as illustrated in FIG. 1B at 32. That is, there will be a first positive pulse during time $t_1$ having a selected value as determined by the power suppy 24 and the recycling capacitor 26 and 28 along with speed of rotation of the wiper arm 12. A second pulse will follow the first pulse of the electic field with the second pulse in a negative direction and having a negative value that is larger than the first value as determined by the recycling capacitors 26 and 28 and the length of the contact segment 18 which as mentioned establishes the time $t_2$. This second pulse will be followed by a third pulse that will be in the same direction as the first pulse and has a value on the order of the first pulse, again as determined by the components of the circuit illustrated in FIG. 1A. This waveform will repeat each time the wipe arm 12 again re-establishes contact with the contact segment 16.

It is desirable for the induced voltage of the treatment coil 22 to remain substantially constant during each of the time intervals $t_1$, $t_2$ and $t_3$. This requires that the corresponding coil current be rising and falling at a uniform rate. A linear current waveform is obtained with an accuracy of plus or minus 5% if the time constant defined by the inductance "L" of the treatment coil 22 and the series circuit resistance "R" as given by the expression $T=L/R$ is $2\frac{1}{2}$ times greater than the rise or fall time, that is, greater than the time interval $t_1$. For this condition and with the ratio $t_1/t_2=5$, the ratio of energy stored in the magnetic field to energy dissipated will be approximately 3.4 thereby providing for substantial recovery of energy from the coil.

In operation, the circuit of FIG. 1A generates a bipolar driving current flowing through the treatment coil 22 to produce a time changing magnetic field. This time changing magnetic field surrounding the treatment coil 22 induces a pulsed electric field into a localized treatment area at which the coil is positioned. The amount of power required to produce a given level of therapeutic effect on living tissue and/or cells has been shown to be on the order of four times lower than a corresponding monopolar circuit of the prior art that generates a two-pulse waveform. Further, the amount of energy consumed during a treatment cycle is reduced by operation of the recycling capacitors 26 and 28. Combined with the use of aluminum rather than copper coil winding, the present invention provides an order-of-magnitude reduction of coil weight for a given volt-seconds of induced electric field compared with prior monopolar drive current configurations.

Figure 2A:
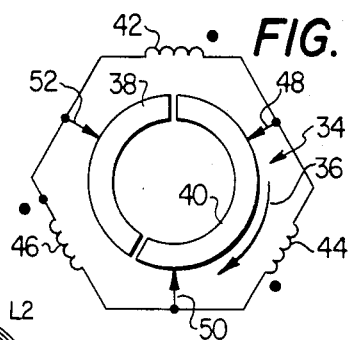
FIG. 2A is a simplified schematic of a three-coil configuration of the present invention to induce a symmetrical distribution of the electric field into the treatment area.

Referring to FIG. 2A, there is shown a schematic representation of rotating switch implementation for generating rotating induced pulsed electric fields in localized treatment areas. The implementation of FIG. 2A may be utilized in conjunction with any suitable source of coil current which may be the circuit of FIG. 1A. Thus, the implementation of FIG. 2A includes a two segment rotary switch 34 rotating in the direction of the arrow 36. The contact segment 38 of the rotary switch 34 is connected to the wiper arm 12 of FIG. 1A through a slip ring or equivalent (not shown) and the contact segment 40 is connected to the connection 21 also through a slip ring or equivalent (not shown). Thus, the circuit of FIG. 2A replaces the treatment coil (or coils) 22 of FIG. 1A.

In FIG. 2A there is shown treatment coils 42, 44 and 46. Treatment coils 42 and 44 are interconnected to a wiper arm 48, treatment coils 44 and 46 are interconnected to a wiper arm 50 and treatment coils 46 and 42 are interconnected to a wipe arm 52. The contact segments 38 and 40 are configured so that the three treatment coils are excited in pairs.

With a three treatment coil configuration, the contact segment 38 occupies 120 degrees of rotation while the contact segment 40 occupies 240 degrees of rotation. As these segments are rotated in the direction of the arrow 36, two of the three treatment coils will be connected to the wiper arm 12. As illustrated in FIG. 2A, coils 42 and 46 are connected to the wiper arm 12 by means of the wiper arm 52. At the same time, these same two treatment coils are connected to the power supply 24 and the recycling capacitors 26 and 28 at the connection 21. This connection is made by means of the wiper arms 48 and 50, respectively. During this time interval the treatment coil 44 will be shorted and will not be contributing to the induced electric field in the treatment area.

As the contact segments 38 and 40 rotate in the direction of the arrow 36, the next two coils energized in the sequence will be treatment coils 42 and 44. When treatment coils 42 and 44 are energized, then the treatment coil 46 is shorted as the contact segment 40 has rotated to make contact with the wiper arms 50 and 52. To complete the sequence, the treatment coils 44 and 46 are connected in parallel and energized while the coil 42 is shorted as the contact segment 40 is rotated to make contact with the wiper arms 48 and 52. It should be noted that it is not a requirement to short circuit the unused coil in this switching sequence since there is little magnetic flux coupling to the unused coil and it therefore has little effect on the fields of the active coils. The shorting sequence is merely a result of the operation of the rotary switch 34.

Rotation of the switch 34 is timed to occur at a rate no greater than the repetition rate of the coil current drive circuit as shown in FIG. 1A. That is, the wiper arm 12 will rotate through all three contact segments 16, 18 and 20 before the rotary switch 34 connects a subsequent pair of treatment coils to the circuit of FIG. 1A. Preferably, rotation of the wiper arm 12 and the rotary switch 34 is synchronized to avoid drive pulses while the switches are transitioning between segments.

Figure 2B:
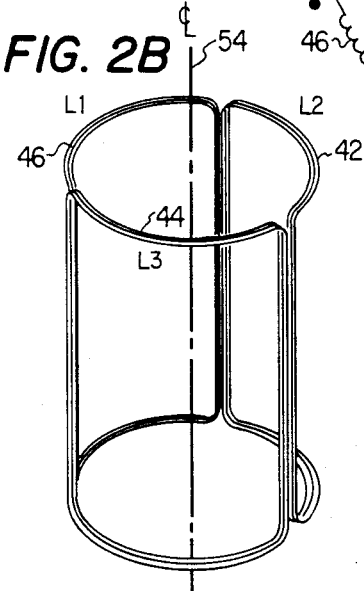
FIG. 2B is an illustration of one configuration of a three-coil apparatus in accordance with the present invention.
Figure 2C:
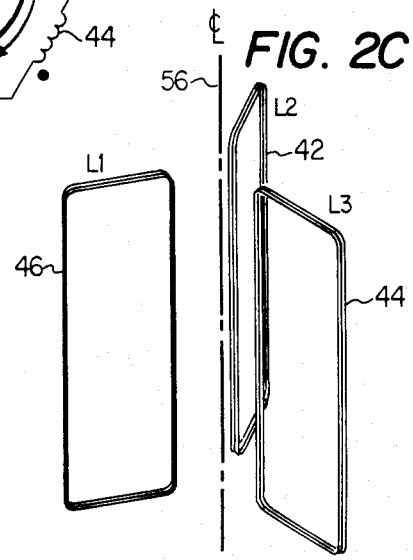
FIG. 2C is an alternate configuration of a three-coil apparatus wherein the induced electric field does not null on the axis and adjacent currents are in an aiding mode.

Referring to FIGS. 2B and 2C, these are isometric illustrations of two arrangements of the treatment coils 42, 44 and 46 arranged about a desired treatment axis of symmetry indicated by the center line 54 in FIG. 2B and the center line 56 in FIG. 2C. The coil configuration of FIG. 2B produces a symmetrical rotating induced electric field having a null near the center line 54. In this configuration currents in adjacent coil wires are in the same direction producing aiding magnetic fields. With reference to FIG. 2C the rotating induced electric fields do not null near the center line 56 although the currents in adjacent coil wires are in the same direction. The coil configuration of FIG. 2B will be recognized as approximately a Helmholtz pair while that of FIG. 2C approximates a toroidal coil. The selection of the coil configuration of either FIG. 2B or FIG. 2C will depend upon the application and the treatment area which is usually near the center line. In either case the axis of symmetry is maintained resulting in a symmetrically induced biological effect while maintaining a constant polarity along the axis in applications where the polarity of the high induced electric field relative to the direction of low induced electric field is desirable.

It will be appreciated from the foregoing description that the direction of the induced electric field with respect to the axis of symmetry is independant of the direction of rotation of the rotary switch 34 of FIG. 2A. Thus, the direction of rotation of the electric field is reversible by reversing the direction of rotation of the switch 34. It should also be recognized that while in FIG. 2B and FIG. 2C three coils are illustrated, the number of treatment coils may be varied and increased, for example, to six or more. Providing more treatment coils enables a more finely graduated advance of the rotating field around the axis of symmetry of the treatment area.

Figure 3:
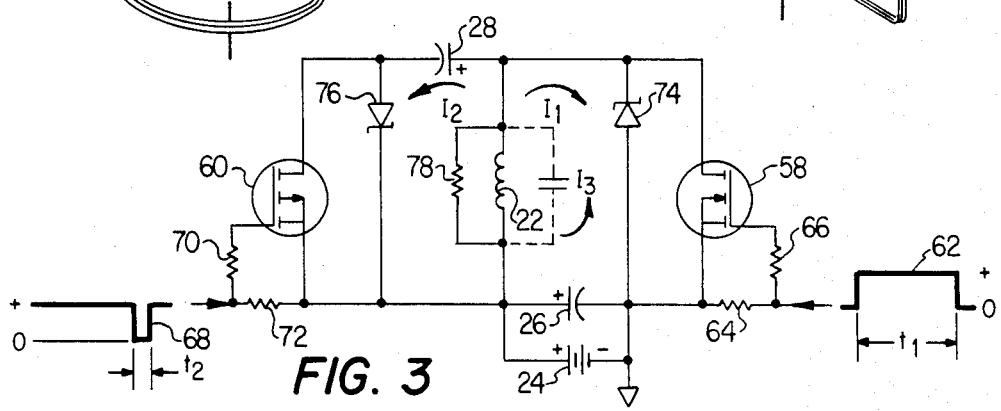
FIG. 3 is a schematic of a bipolar current drive circuit in accordance with the present invention.

Referring now to FIG. 3, there is shown an implementation of a bipolar current drive in accordance with the present invention utilizing field effect transistors as the switching element in place of the rotary switches of FIG. 1A. In the circuit of FIG. 1 the treatment coil 22, the recycling capacitors 26 and 28 and the power supply 24 are the same as those illustrated in FIG. 1A. The function of the rotary switch 10 of FIG. 1A has been replaced by an N-channel field effect transistor (FET) 58 and a P-channel field effect transistor (FET) 60. Basically, the FET 58 replaces the contact segment 16 and the FET 60 replaces the contact segment 18 of FIG. 1A. The FET 58 is switched "on" for a time interval $t_1$ by means of a drive voltage 62 applied to a gate drive circuit including resistor 64 and 66. Similarly, the FET 60 is switched on for a time interval $t_2$ by a voltage 68 by means of a gate drive circuit including resistors 70 and 72. It should be noted that the time intervals $t_1$ and $t_2$ are the same as illustrated in FIG. 1B.

To protect the FET 58 during operation of the circuit of FIG. 3 a Zener diode is connected between the drain and source terminals of the FET. This protects the FET from excessive transient voltages created by the collapsing field of the treatment coil 22 during switching of the current flow. Similarly, a Zener diode 76 is connected between the drain and source terminals of the FET 60 for protection from excessive transient voltages.

In operation, switching "on" the FET 58 produces a current flow $I_1$ from the recycling capacitor 26 through the treatment coil 22 increasing at a rate as illustrated by the waveform segment 30a of FIG. 1B. The current flowing through the treatment coil 22 reaches a maximum at the end of the time interval $t_1$ as controlled by the duration of the drive voltage 62. At this point the FET 58 is turned "off" and the FET 60 is simultaneously turned "on" by means of the applied voltage 68. Current flow through the treatment coil 22 is now illustrated by the waveform segment 30b of FIG. 1B during time interval $t_2$. This current is indicated in FIG. 3 by $I_2$ and flows to the recycling capacitor 28 via diode 76 in its forward direction. Current flows into the capacitor 28 until it reaches the zero axis level and then switches and flows from the capacitor via FET 60 into the treatment coil 22 until the FET 60 is switched "off" at the end of the time interval $t_2$. With both the FET 58 and the FET 60 switched "off", stored energy of the magnetic field surrounding the treatment coil 22 generates a current flow through the Zener diode 74 in its forward direction as indicated by the arrow $I_3$ recharging the recycling capacitor 26. This continues until the magnetic field has completely collapsed and zero current is flowing through the circuit. The time required for the current $I_3$ to return to a zero value is defined by the time interval $t_3$ of FIG. 1B.

Because the Zener diode 74 has a small forward voltage drop as a result of the current flow $I_3$, a small amount of stored energy will remain in the magnetic field surrounding the treatment coil 22 at the nominal end of the time interval $t_3$. This will result in a damped oscillation at a frequency determined by the inductance of the treatment coil 22 and a small stray capacitance associated therewith. To provide critical damping of this oscillation a resistor 78 is connected in parallel with the treatment coil 22.

It will be appreciated that the circuit of FIG. 3 functions in a manner similar to the circuit of FIG. 1A to generate a time changing magnetic field to induce a pulsed electric field into a localized treatment area by means of the treatment coil 22. The waveform of the pulsed electric field will have a first pulse in a positive direction having a selected value. This first pulse will be followed by a second pulse in the negative direction having a second value larger than the value of the first pulse. This second pulse will in turn be followed by a third pulse in the positive direction again having a value on the order of the first pulse. This waveform is illustrated at 32 in FIG. 1B. By means of the treatment coil 22 in the circuit of FIG. 3 there is provided a method and apparatus for noninvasive treatment of biological living tissues and/or cells in a body.

Figure 4:
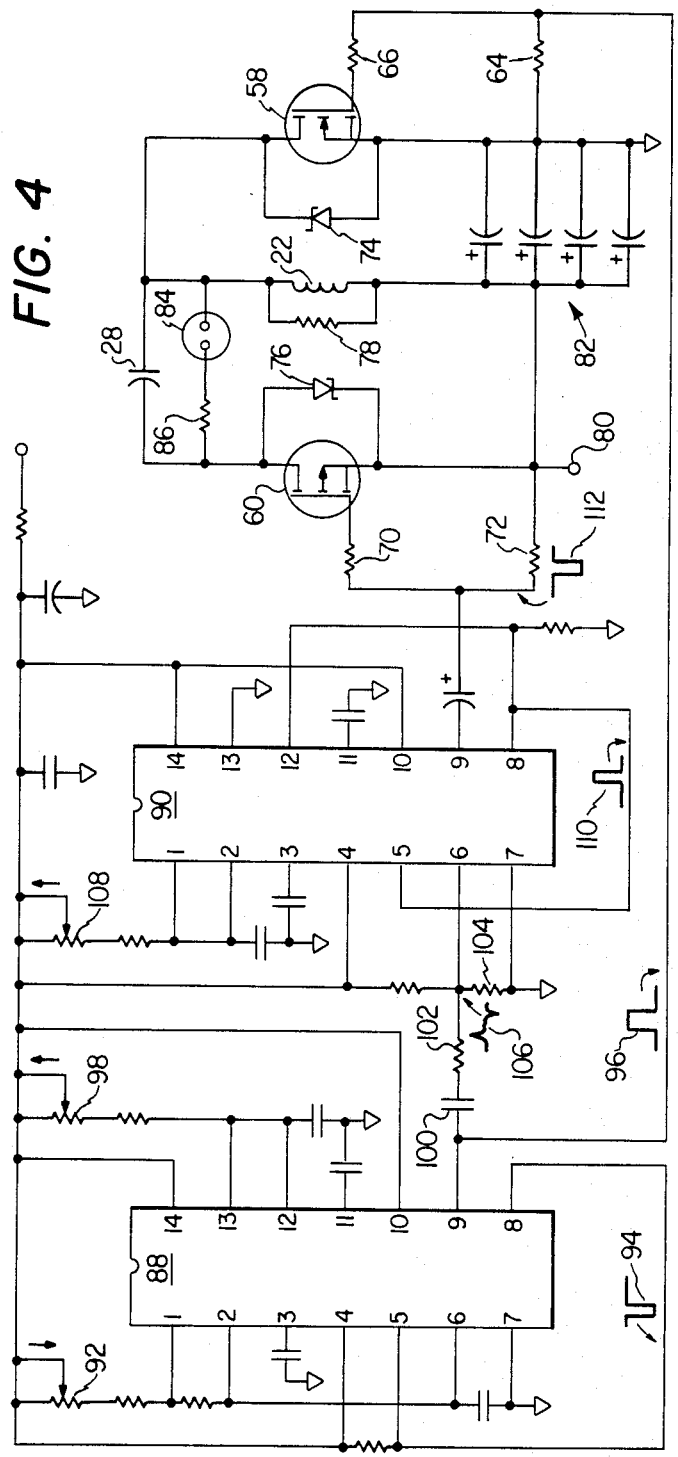
FIG. 4 is another embodiment of a bipolar current drive circuit using low power CMOS components.

Referring to FIG. 4, there is shown a schematic of an electronic bipolar current drive and energy recovery circuit including timing circuits for generating the drive voltages for FET transistors 58 and 60. In FIG. 4 the circuit of FIG. 3 with reference to the field effect transistors 58 and 60 is repeated. Thus, for the FET 58 there is the gate drive circuit including resistors 64 and 66 and for the FET 60 there is the gate drive circuit including resistors at 70 and 72. Transient high voltage protection provided by Zener diodes 74 and 77 is also included in FIG. 4 connected to the FET 58 and the FET 60, respectively. Also illustrated in FIG. 4 is the treatment coil 22 and the recycling capacitor 28. The recycling capacitor 26 has been replaced by a capacitor network 82 comprising four capacitors in parallel. Also the power supply 24 has been replaced with an external power supply connected to a terminal 80. Parallel with the treatment coil 22 is the resistor 78.

Also illustrated in FIG. 4 is a gas discharge indicating light 84 in series with a resistor 86 ad connected in parallel with the recycling capacitor 28. This light gives an indication that the treatment coil 22 is being energized and is neither open circuited nor short circuited.

To provide the drive voltages to the FET 58 and the FET 60, there is provided an integrated circuit 88 and an integrated circuit 90 which are each dual timers (such as the type 7556). The first half of the integrated circuit 88 (pins 1 through 6) operates as an astable multivibrator that controls the repetition frequency of the drive pulses to FETs 58 and 60. Typically, the pulse repetition frequency will vary between 30 and 120 pulses per second and is adjustable by means of a variable resistor 92.

An output of the astable multivibrator is shown by the waveform 94 and triggers a monostable multivibrator that comprises the second half of the integrated circuit 88 (pins 8 through 13). This monostable multivibrator generates an output as indicated by the waveform 96 that drives the gate of the FET 58. Typically, the pulse width of the waveform 96 varies between 250 and 750 microseconds and is adjustable by means of a variable resistor 98.

In addition to driving the FET 58 the output of the monostable multivibrator is applied to a differentiator circuit including a capacitor 100 and resistors 102 and 104 to generate a trigger pulse (the waveform 106) to trigger a monostable multivibrator comprising the first half of the integrated circuit 90 (pins 1 through 6). This monostable multivibrator generates an output havng the desired pulse width for driving the FET 60. The pulse width is adjusted within the range of 50 to 150 microseconds by means of an adjustable resistor 108. The pulse output of the monostable multivibrator comprising the first half of the integrated circuit 90 as illustrated by the waveform 110 and is applied to an inverter comprising the second half of the integrated circuit. The inverted pulse output of the inverter is indicated by the waveform 112 and is applied to the drive circuit for the FET 60.

Operationally, the circuit of FIG. 4 is similar to the circuit of FIG. 3. The FET 58 and the FET 60 in conjunction with the integrated circuits 88 and 90 operate to produce a time changing magnetic field to induce a pulsed electric field into a localized treatment area by means of the treatment coil (or coils) 22. The three-pulse waveform of this electric field is illustrated in FIG. 1B.

As an alternate embodiment to FIG. 3 the treatment coil (or coils) 22 is replaced by the circuit of FIG. 2A. To be consistent with the FET switching of FIG. 3 the rotary switch 34 may also be replaced with semiconductor switching devices. This modification of FIG. 3 results in a rotation of the electric field by means of the treatment coils 42, 44 and 46 to produce a time-averaged symmetry of stimulation in the treatment area for bone growth and repair.

Similarly, the circuit of FIG. 4 is modified to replace the treatment coil 22 with the circuit of FIG. 2A. Again, semiconductor switching replaces the rotary switch 34 as illustrated in FIG. 2A. The energy-saving features as described with reference to FIG. 1A will also be found in these modifications of FIGS. 3 and 4.

While the present invention has been described with respect to specific details thereof, it should be understood that various changes and modification will be suggested to one skilled in the art to which the invention relates, and it is intended to encompass those changes and modifications which fall within the scope of the appended claims.

I claim:

1. Apparatus for noninvasive treatment of biological tissue comprising:
   means for generating a bipolar driving current;
   means responsive to the bipolar driving current to induce pulse electric fields that repeat at spaced time intervals into a localized treatment area, said means to induce including means for generating an electric field waveform that has a first pulse in a first direction having a selected value followed by a second pulse in a second direction having a second value larger than the value of the first pulse, and followed by a third pulse in the first direction having a value on the order of the value of the first pulse, where the waveform is followed by an inactive interval and repeats for a selected number of repetitions; and
   means connected to said means to induce a pulse electric field to couple the energy of the first pulse to generate the second pulse and couple the energy from the second pulse to generate the third pulse and store the energy from the third pulse.

2. Apparatus for noninvasive treatment of biological tissue as set forth in claim 1 wherein said means to induce a pulse electric field includes means for recovering from the third pulse greater energy than the energy dissipated during the first, second and third pulses.

3. Apparatus for noninvasive treatment of biological tissue as set forth in claim 2 wherein said means to induce pulse electric fields includes at least one magnetic coil for generating a time changing magnetic field.

4. Apparatus for noninvasive treatment of biological tissue as set forth in claim 2 wherein the magnetic coil is wound from an electrical conductor of aluminum.

5. Apparatus for noninvasive treatment of biological tissue as set forth in claim 3 wherein said means to couple includes a first low voltage capacitor connected to said magnetic coil to be discharged during the first pulse timer interval, and charged during the third pulse time intervals, and a high voltage capacitor connected to said magnetic coil during the second pulse time interval.

6. Apparatus for noninvasive treatment of biological tissue as set forth in claim 5 wherein said means to couple further includes means to switch the low voltage capacitor to the magnetic coil during the first and third pulse time intervals and for swiching the high voltage capacitor to the magnetic coil during the second pulse time interval.

7. Apparatus for noninvasive treatment of biological tissue as set forth in claim 6 including means for timing the switching of the low voltage capacitor to the coil during the first and third pulse time intervals and for timing the switching of the high voltage capacitor to said coils during the second pulse time interval.

8. Apparatus for noninvasive treatment of biological tissue comprising:
   means for generating a driving current;
   a plurality of magnetic coils arranged in the area of desired treatment and responsive to the driving current to induce a pulse electric field that repeats at spaced time intervals into the localized treatment area, wherein the electric field waveform has a first pulse in a first direction having a selected value followed by a second pulse in a second direction having a value larger than the first pulse, and followed by a third pulse in the first direction having a value on the order of the first pulse, where the waveform is followed by an inactive interval and repeats at spaced time intervals for a selected number of repetitions; and means connected to said coils to couple the energy of the first pulse to generate the second pulse and couple the energy from the second pulse to generate the third pulse and to store the energy from the third pulse.

9. Apparatus for noninvasive treatment of biological tissue as set forth in claim 8 wherein three magnetic coils are positioned in the treatment area to induce a symmetrical distribution of the electric field in the treatment area, and wherein the three coils are arranged at equal angles around the desired axis of symmetry.

10. Apparatus for noninvasive treatment of biological tissue as set forth in claim 9 including means connected between said means for generating a driving current and said coils to connect said coils to the means for generating in sequential pairs in a rotating sequence.

11. Apparatus for noninvasive treatment of biological tissue as set forth in claim 10 wherein the three coils are engerized in sequential pairs with the induces electric fields resulting from the aiding magnetic fields in adjacent driven pairs.

12. Apparatus for noninvasive treatment of biological tissue as set forth in claim 8 including means for coupling said means for generating to said coils to induce the pulse electric field to rotate through 120° as each sequential pair of coils is connected to said means for generating to produce a time averaged symmetry of the magnetic fields.

13. A method of noninvasive treatment of biological tissue comprising the steps of:

generating a driving current; and in response to the driving current, generating a time changing magnetic field to induce time displaced periodically repetitive pulse electric fields into a localized treatment area.

wherein the waveform of the time displaced periodically repetitive pulse electric field has a first pulse in a first direction having a selected value followed by a second pulse in a second direction having a second value larger than the value of the first pulse, followed by a third pulse in the first direction having a value on the order of the first pulse where the waveform is followed by an inactive interval and then repeats for a selected number of repetitions.

14. The method of noninvasive treatment of biological tissue as set forth in claim 1 wherein the volt-second product of the first pulse substantially equals the volt-second product of the third pulse and the magnitude of the volt-second product of the second pulse substantially equals the sum of the volt-second products of the first and third pulses.

15. A method of noninvasive treatment of biological tissue as set forth in claim 1 wherein the first pulse is sustained in the first direction for a preset time interval, the second pulse is sustained in the second direction for a preset time interval less than the first pulse.

16. A method of noninvasive treatment of biological tissue as set forth in claim 1 including rotating the electric field to produce a time averaged symmetry of stimulation in the treatment area for bone growth and repair.

* * * * *